(12) United States Patent
Wendland et al.

(10) Patent No.: US 11,083,849 B2
(45) Date of Patent: Aug. 10, 2021

(54) AUTO-INJECTOR

(71) Applicant: Sanofi-Aventis Deutschland GmbH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 192 days.

(21) Appl. No.: 15/778,965

(22) PCT Filed: Nov. 21, 2016

(86) PCT No.: PCT/EP2016/078241
§ 371 (c)(1),
(2) Date: May 24, 2018

(87) PCT Pub. No.: WO2017/089253
PCT Pub. Date: Jun. 1, 2017

(65) Prior Publication Data
US 2018/0353697 A1     Dec. 13, 2018

(30) Foreign Application Priority Data
Nov. 27, 2015   (EP) ..................................... 15196665

(51) Int. Cl.
*A61M 5/315*     (2006.01)
*A61M 5/20*      (2006.01)

(52) U.S. Cl.
CPC .... *A61M 5/31511* (2013.01); *A61M 5/31576* (2013.01); *A61M 5/31578* (2013.01);
(Continued)

(58) Field of Classification Search
CPC ......... A61M 2005/31518; A61M 2005/14506; A61M 2005/31588; A61M 5/1454; A61M 5/145; A61M 5/1542
See application file for complete search history.

(56) References Cited

U.S. PATENT DOCUMENTS

2007/0073236 A1   3/2007   Mernoe et al.
2014/0035604 A1   2/2014   Paul et al.

FOREIGN PATENT DOCUMENTS

WO     WO 2013/153041     10/2013

OTHER PUBLICATIONS

International Preliminary Report on Patentability in International Application No. PCT/EP2016/078241, dated May 29, 2018, 7 pages.
(Continued)

*Primary Examiner* — Nathan R Price
*Assistant Examiner* — Tania Ismail
(74) *Attorney, Agent, or Firm* — Fish & Richardson P.C.

(57) ABSTRACT

An auto-injector for delivering a liquid medicament comprising: a housing arranged to contain a syringe and a piston for sealing the syringe and displacing the medicament, the housing having a proximal end and a distal end intended to be applied against an injection site, wherein the syringe comprises: a plurality of plunger elements arranged along a length of the syringe between the proximal end of the housing and the piston, each of the plurality of plunger elements having a longitudinal axis; and a cord arranged to connect the plurality of plunger elements, wherein the plunger elements are configured to become aligned along their axes to push the piston towards the distal end to displace the medicament when the cord is acted on by a driving force.

20 Claims, 6 Drawing Sheets

(52) U.S. Cl.
CPC ....... *A61M 5/31585* (2013.01); *A61M 5/2033* (2013.01); *A61M 2005/206* (2013.01); *A61M 2005/31518* (2013.01); *A61M 2005/31588* (2013.01)

(56) References Cited

OTHER PUBLICATIONS

International Search Report and Written Opinion in International Application No. PCT/EP2016/078241, dated Feb. 27, 2017, 12 pages.

AUTO-INJECTOR

CROSS REFERENCE TO RELATED APPLICATIONS

This application is a U.S. national stage application under 35 USC § 371 of International Patent Application No. PCT/EP2016/078241, filed on Nov. 21, 2016, which claims priority to European Patent Application No. 15196665.2, filed on Nov. 27, 2015, the entire contents of each of which are incorporated herein by reference.

TECHNICAL FIELD

The disclosure generally relates to an auto-injector.

BACKGROUND

Current therapies delivered by means of self-administered injections include drugs for diabetes (both insulin and new GLP-A class drugs), migraine, hormone therapies, anticoagulants etc. Administering an injection is a process which presents a number of risks and challenges for user and healthcare professionals, both mental and physical.

Conventional injection devices typically fall under two categories—manual devices and auto-injectors. In a conventional manual device, a user must provide a force to drive a liquid medicament out of the device, e.g. by depressing a plunger. There are numerous disadvantages inherent with user of a manual device. For example, if the user stops depressing the plunger, less than a full dose of the liquid medicament may be delivered. Furthermore, the force required to depress the plunger may be problematic for elderly users or those with dexterity problems, which may lead to trembling or shaking when aligning or the injection and/or while administering the dose of the liquid medicament. In addition, the extension of the button or plunger of manual devices may be too great. Thus it can be inconvenient for the user to reach a fully extended button.

Auto-injectors aim to make self-administration of injected therapies easier for users. Auto-injectors are devices which completely or partially replace activities involved in medicament delivery of manual devices. These activities may include removal of a protective syringe cap, insertion of a needle into a patient's skin, injection of the medicament, removal of the needle, shield of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth.

In some auto-injectors plunger arrangements for provided for exerting a force to push the liquid medicament out of the syringe to be delivered to the user. These plunger arrangements typically add to the length of the housing of the auto-injector.

SUMMARY

According to an aspect, there is provided an auto-injector for delivering a liquid medicament comprising: a housing arranged to contain a syringe and a piston for sealing the syringe and displacing the medicament, the housing having a proximal end and a distal end intended to be applied against an injection site, wherein the syringe comprises: a plurality of plunger elements arranged along a length of the syringe between the proximal end of the housing and the piston, each of the plurality of plunger elements having a longitudinal axis; and a cord arranged to connect the plurality of plunger elements, wherein the plunger elements are configured to become aligned along their axes to push the piston towards the distal end to displace the medicament when the cord is acted on by a driving force.

This particular plunger arrangement in the auto-injector allows for a more compact and easily portable auto-injector.

Each of the plurality of plunger elements may comprise a longitudinal hole, and the cord may be threaded through the longitudinal holes of the plurality of plunger elements to connect the plurality of plunger elements.

The plurality of plunger elements may be in a stacked arrangement in an initial state.

The auto-injector may further comprise a driving actuator connected to the cord so as to provide the driving force for acting on the cord. The use of a driving actuator helps ensure a more constant force, compared to manually acting on the cord.

The driving actuator may comprise a drive spring releasably compressed by an activation arrangement, and wherein when upon activating the activation arrangement the drive spring may be released such that it decompresses to provide the driving force for acting on the cord.

The drive spring and the activation arrangement may be arranged at a side wall of the housing.

The auto-injector may further comprise a projection is provided at the side wall of the housing arranged to limit decompression of the drive spring.

The auto-injector may further comprise a slot provided at the side wall of the auto-injector through which the activation arrangement protrudes, so as to allow manual operation of the activation arrangement.

The activation arrangement may comprise an electric motor.

The electric motor may be arranged to wind the cord during acting on of the cord.

Each of the plurality of plunger elements may have a circular disc shape.

Edges of the plurality of plunger elements adjacent the ends of the longitudinal holes may be rounded or chamfered.

Adjacent plunger elements in the plurality of plunger elements may be connected by a plurality of elastic elements, the plurality of elastic elements being arranged to stretch as the plunger elements become aligned along their axes.

A medicament may be included in the syringe.

According to another aspect, there is provided a method of actuating an auto-injector having a plurality of plunger elements arranged with longitudinal axes arranged generally laterally to a longitudinal axis of the auto-injector, comprising the step of: applying a force in the longitudinal direction of the auto-injector to at least one of the plurality of plunger elements to cause realignment of the at least one of the plurality of plunger elements so that the longitudinal axis of the plunger element is aligned generally parallel to the longitudinal axis of the auto-injector.

These and other aspects will be apparent from and elucidated with reference to the embodiments described hereinafter.

BRIEF DESCRIPTION OF THE DRAWINGS

Embodiments will now be described, by way of example only, with reference to the accompanying drawings, in which.

Reference will now be made in detail to the embodiments, examples of which are illustrated in the accompanying drawings, wherein like reference numerals refer to like elements throughout.

DETAILED DESCRIPTION

Figure 1A:
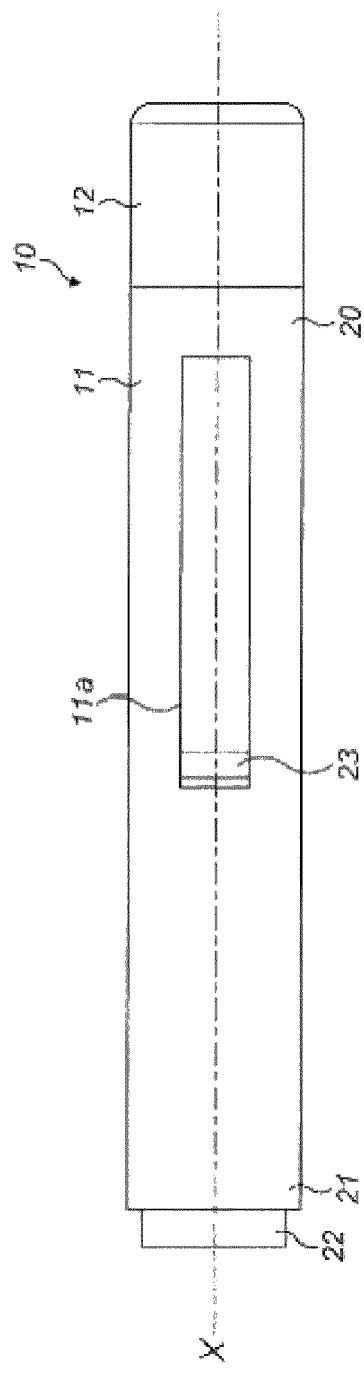
FIGS. 1A and 1B are side-on views of an auto-injector device according to an embodiment.

An auto-injector device with a plunger arrangement is provided. The plunger arrangement is arranged in the auto-injector device such that upon activation, it can push a piston in a syringe contained in the auto-injector device, so as to deliver liquid medicament contained inside the syringe.

The plunger arrangement includes a plurality of circular-disk shaped plunger elements arranged along the syringe such that they are stacked together. Each plunger element comprises a longitudinal axis and a longitudinal hole through which a cord is threaded through for connecting all the plunger elements. The edges of the plunger elements adjacent the ends of the holes are rounded or otherwise chamfered. When the cord is acted on by a driving force, the plunger elements rotate and become aligned along their longitudinal axes. The aligning of the plunger elements pushes the piston towards a syringe opening and displaces the liquid medicament through a hollow injection needle.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
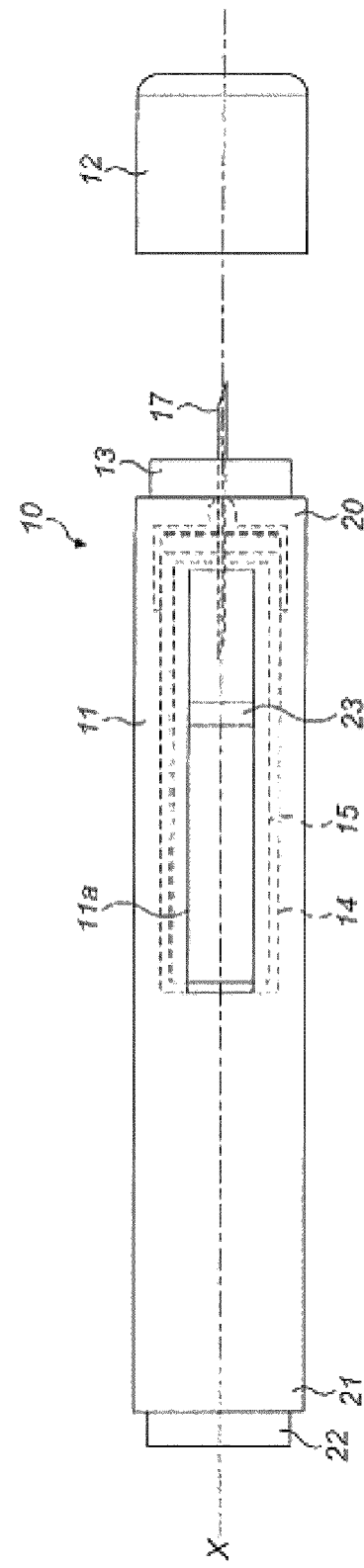

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
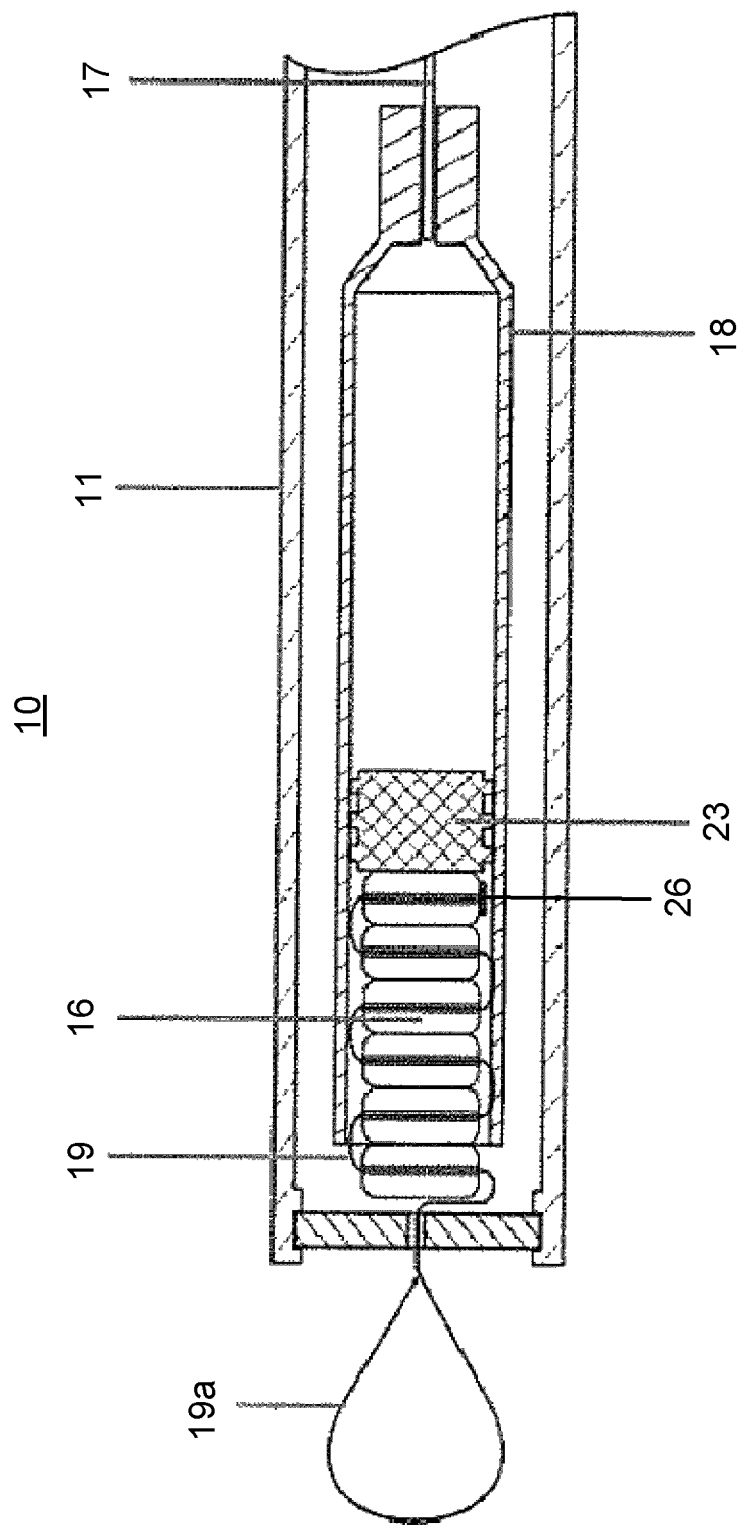
FIG. 2 is a cross-sectional view of an auto-injector device in an initial state, according to a first embodiment.

FIG. 2 is a cross-sectional view of an injector device in an initial state, according to a first embodiment.

FIG. 2 shows an auto-injector device 10 comprising a body 11 and a housing 11. The housing 11 is arranged to contain a syringe 18 having a hollow injection needle 17 and a piston, stopper or bung 14 for sealing the syringe 18 and displacing liquid medicament 16 that is contained within the syringe 18. The housing 11 comprises a proximal end and a distal end intended to be applied against an injection site during injection of the liquid medicament 16. In the present embodiment, the distal end of the housing 11 comprises an orifice (not shown in the drawing) for exposing the hollow injection needle 17.

A plurality of plunger elements 16 are arranged along a length of the syringe between the proximal end of the housing 11 and the piston 23, each of the plurality of plunger elements 16 having a longitudinal axis and comprising a longitudinal hole. In the present embodiment, each of the plurality of plunger elements 16 are circular disc-shaped in order to conform to the cylindrical shape of the syringe 18. The holes in each of the plurality of plunger elements 16 are arranged longitudinally (i.e. along a diameter, crossing the centre) in the circular disc-shaped plunger element.

A cord 19 is threaded through the longitudinal holes of the plurality of plunger elements 16 so as to connect the plurality of plunger elements 16. The cord 19 is made of generally inextensible, inductile, or inelastic material, such as surgical steel, piano wire or kite line, so as to allow the plurality of plunger elements 16 to exist in the initial state in which they are in a stacked arrangement as shown in FIG. 2, i.e. their longitudinal axes are each perpendicular to an axis of the syringe 18 without applying any significant force to the piston 23, in the absence of any actuation force acting on the cord 19.

When the cord 19 is acted on by a driving force (i.e. being pulled by the driving force in the present embodiment), the cord 19 is tensioned by the driving force F which causes the plurality of plunger elements 16 to rotate and become aligned along their longitudinal axes. This will be explained in further detail with respect to FIG. 3.

In addition, as shown in FIG. 2, from the cross-sectional view the plurality of plunger elements 16 have rounded corners around their edges. Hence, in the present embodiment, the pivot point between two plunger elements in the initial state is a point of contact between the two plunger elements that is closest to the hole openings at which the cord is threaded through to connect both plunger elements.

This pivot point, as compared to a pivot point of a configuration in which the plurality of plunger elements have straight edges, provides a greater angle θ between the moment arm r (i.e. the distance from the pivot point to the point where the driving force from the cord F acts) and the driving force F, which initially acts in a perpendicular direction to the longitudinal axis of the plunger element to be rotated. By τ=r×F, the torque τ is increased when this angle θ increases. As a result, compared to the configuration in which the plurality of plunger elements have straight edges, the feature of rounded corners allows for more efficient rotation of the plurality of plunger elements so that they can be more easily aligned along their longitudinal axes.

A securing means 26 is provided at one end of the cord 19 in order to secure the plurality of plunger elements 16 in the cord 19. In the present embodiment, the securing means 26 is an end tab which is larger than an opening of a longitudinal hole of the plurality of plunger elements 16. As shown in FIG. 2, a loop 19a is provided at the other end of the cord 19 as a simplified representation of a driving force that is provided to act on the cord 19 towards the proximal end of the housing 11.

It is to be understood that the loop 19a as illustrated in FIG. 2 is merely a simplified representation and in some alternative embodiments it may be replaced by any driving actuator that could provide a driving force F for acting on the cord 19. As will be described with respect to FIG. 3, this driving force F is provided by a drive spring and an activation arrangement.

In the initial state of the plunger arrangement in the auto-injector device 10 as illustrated in FIG. 2, the plurality of plunger elements 16 are in a stacked arrangement such that the longitudinal axes of the plurality of plunger elements 16 are perpendicular to the axis of the auto-injector device 10. The longitudinal axes of the plurality of plunger elements 16 are also parallel to each other. As will be described with reference to FIGS. 3 and 4 in the following, upon acting on of the cord 19 by a driving force provided by a driving actuator, the plurality of plunger elements 16 become aligned along their longitudinal axes.

Figure 3:
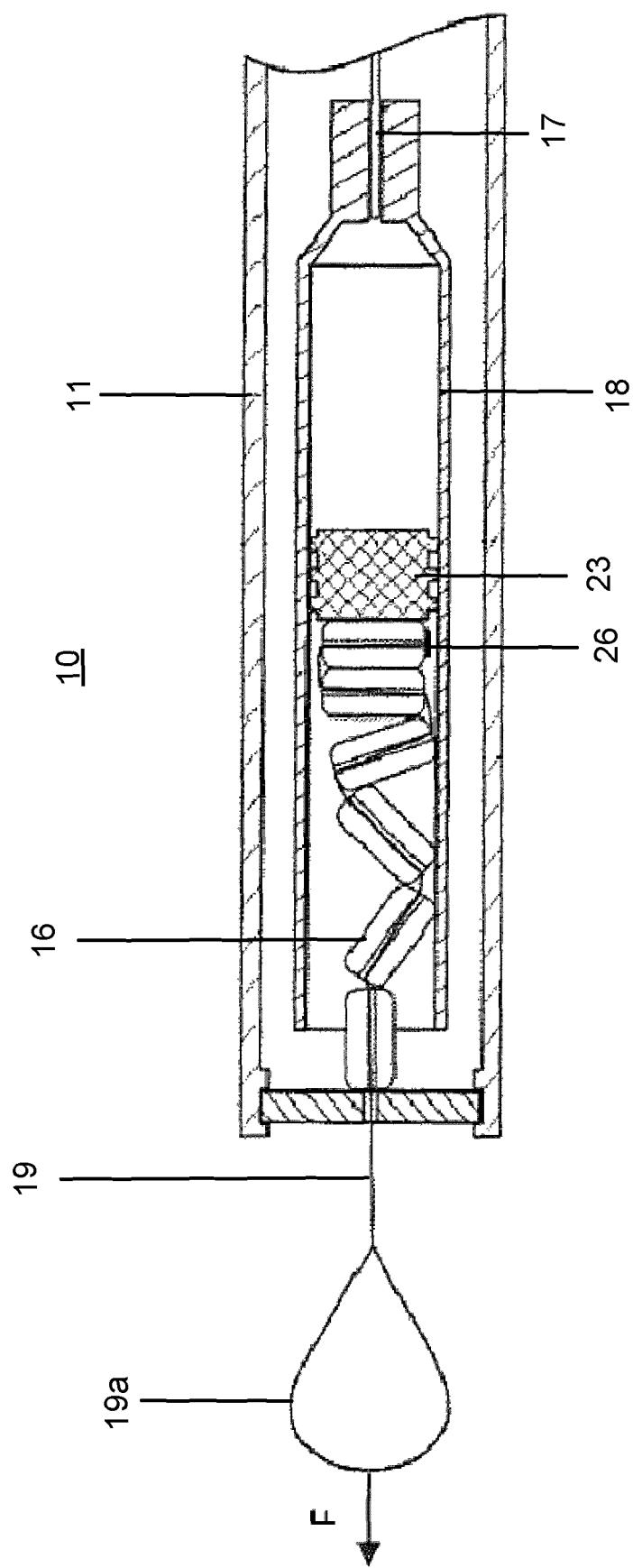
FIG. 3 is a cross-sectional view of the auto-injector device of FIG. 2 in an intermediate state.

FIG. 3 is a cross-sectional view of the auto-injector device of FIG. 2 in an intermediate state.

As shown in FIG. 3, a driving force F is acting on the loop 19a to the right, i.e. acting on the securing means provided at the end of the cord 19 towards the proximal end of the housing 11. As the cord 19 is tensioned by the driving force F, the plurality of plunger elements 16 become aligned along their longitudinal axes, starting with the plunger element 22 that is closest to the proximal end of the housing 11, as shown in FIG. 3.

Since the diameters of the plurality of plunger elements 16 are larger than their heights, when the plurality of plunger elements 16 become more and more aligned along their longitudinal axes, the piston 23 is pushed towards the distal end of the housing 11 so as to allow more space within the syringe 18 to accommodate the plurality of plunger elements 16 that are becoming increasingly aligned along their axes. At the same time, the movement of the piston 23 displaces the liquid medicament to a user through the hollow injection needle 17.

The intermediate state as shown in FIG. 3 demonstrates a state in which the plunger element 22 that is closest to the proximal end of the housing 11 becomes fully aligned such that its longitudinal axis aligns with the axis of the syringe 18, and the longitudinal axes of a number of other plunger elements that are more proximate to the proximal end of the housing 11 becoming more aligned along the axis of the syringe 18. As the driving force F continues to act on the loop 19a of the cord 19, the auto-injector device 10 reaches the final state in which all of the plurality of plunger elements 16 are aligned along their axes. This is illustrated in FIG. 4.

Figure 4:
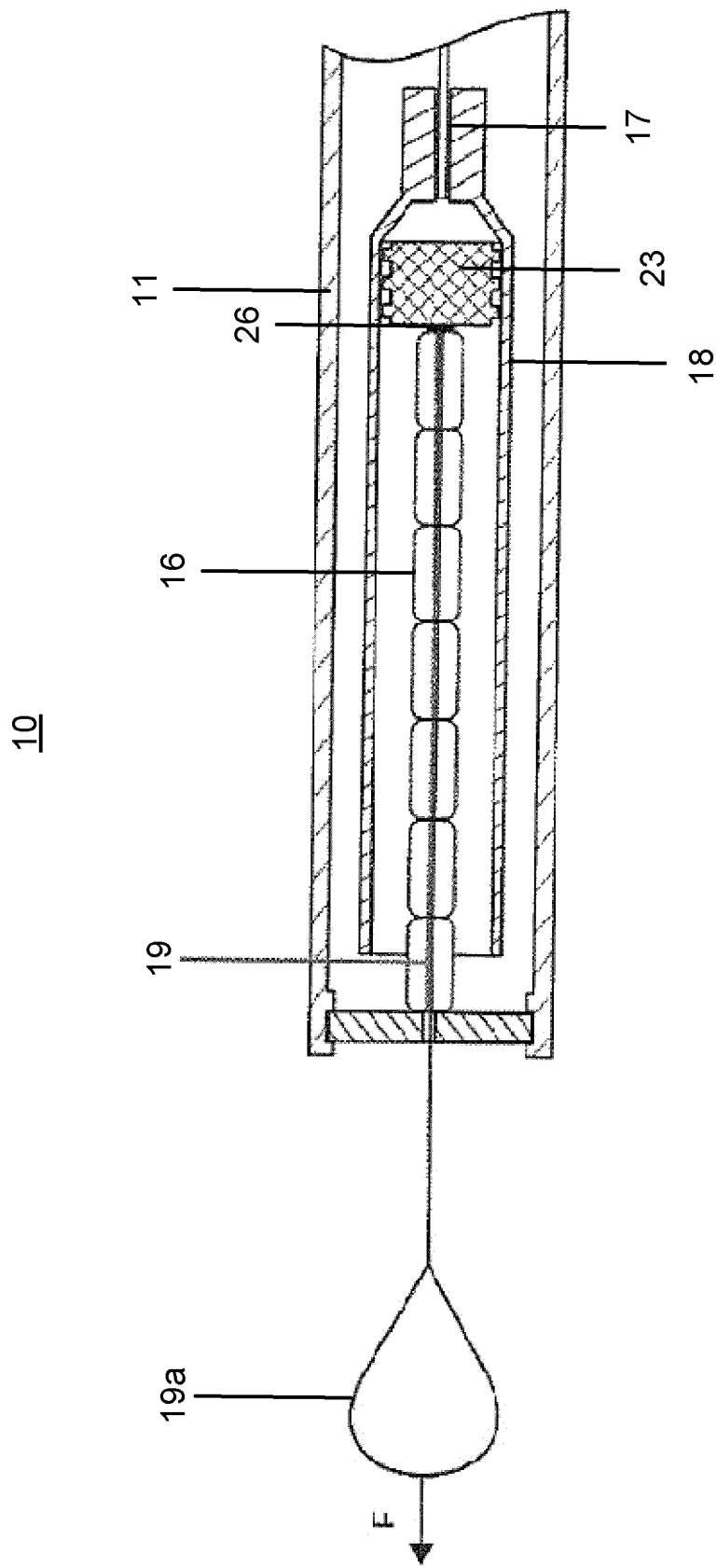
FIG. 4 is a cross-sectional view of the auto-injector device of FIGS. 2 and 3 in a final state.

FIG. 4 is a cross-sectional view of the auto-injector device of FIGS. 2 and 3 in a final state.

As shown in FIG. 4, the driving force F continues to act on the loop 19a to the left and acting on the cord 19 towards the proximal end of the housing 11. All of the plurality of plunger elements 16 become fully aligned along their longitudinal axes.

In the present embodiment, when all of the plurality of plunger elements 16 are aligned along their longitudinal axes, they are also aligned with the axis of the syringe 18. This particular arrangement that the plunger elements 16 are aligned along the axis of syringe 18 ensures a central and relatively constant force acting on the piston 23 to push the liquid medicament out of the hollow injection needle 17, such that the liquid medicament is delivered to the patient in a steady rate.

It is advantageous that, when the plurality of plunger elements 16 are aligned along their longitudinal axes, the diameters of the plurality of plunger elements correspond to the distance between the proximal end of the housing 11 and the piston 23, such that a maximum amount of liquid medicament is pushed out of the syringe 18 through the hollow injection needle 17. This ensures that the auto-injector device 10 does not deliver an incomplete dose. This arrangement is illustrated in FIG. 4.

Figures 5A, 5B, 5C:
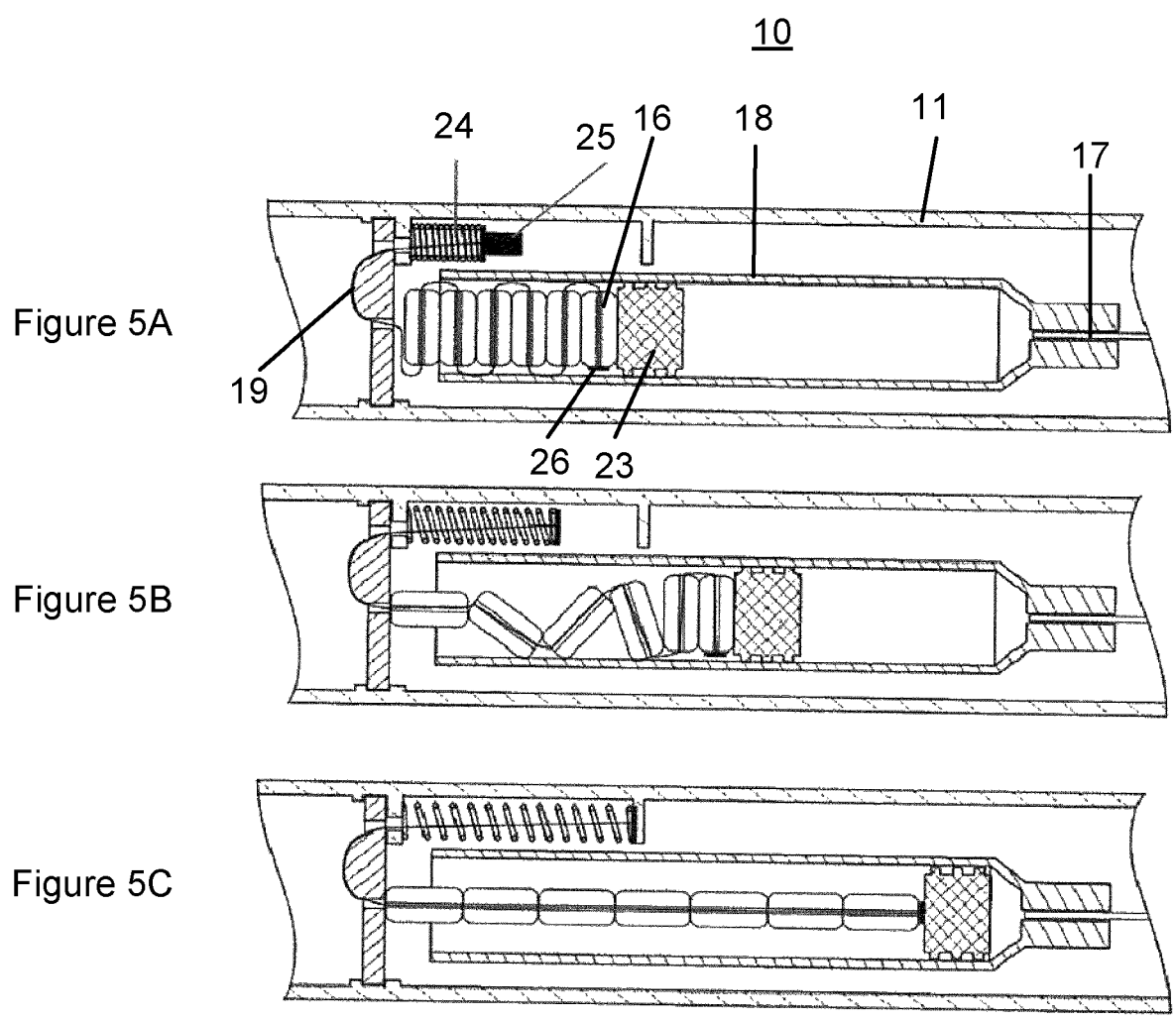
FIGS. 5A, 5B, and 5C are cross-sectional views of an auto-injector device according to a second embodiment in an initial state, an intermediate state, and a final state.

FIG. 5A is a cross-sectional view of an auto-injector device in an initial state, according to a second embodiment.

FIGS. 5B and 5C are cross-sectional views of the auto-injector device of FIG. 5A in an intermediate state and a final state respectively.

The second embodiment as illustrated in FIGS. 5A to 5C is similar to the first embodiment as shown in FIGS. 2 to 4. In the second embodiment, the loop 19a of the cord 19 is replaced by a drive spring 24 that is arranged at a side wall of the housing 11, along with an activation arrangement 25. The drive spring 24 is in a compressed state in the initial state, as shown in FIG. 5A.

Similar to the first embodiment, in the second embodiment the auto-injector device 10 comprises a housing 11. The housing 11 is arranged to contain a syringe 18 having a hollow injection needle 17 and a piston 23 for sealing the syringe 18 and displacing liquid medicament 16 that is contained within the syringe 18. The housing 11 comprises a proximal end and a distal end intended to be applied against an injection site during injection of the liquid medicament. In the present embodiment, the distal end of the housing 11 comprises an orifice for exposing the hollow injection needle 17.

A plurality of plunger elements 16 are arranged along a length of the syringe 18 between the proximal end of the housing 11 and the piston 23, each of the plurality of plunger elements 16 having a longitudinal axis and comprising a longitudinal hole. In the present embodiment, each of the plurality of plunger elements 16 is circular disc-shaped in order to conform to the cylindrical shape of the syringe 18. The holes in each of the plurality of plunger elements 16 are arranged longitudinally (i.e. along a diameter, across the centre) in the circular disc-shaped plunger element.

A cord 19 is threaded through the longitudinal holes of the plurality of plunger elements 16 so as to connect the plurality of plunger elements 16. The cord 19 is made of generally inextensible or inelastic material, such as surgical steel, piano wire or kite line, so as to allow the plurality of plunger elements 16 to exist in the initial state in which they are in a stacked arrangement as shown in FIG. 5A, i.e. their longitudinal axes are each perpendicular to an axis of the syringe 18 without applying any significant force to the piston 23, in the absence of any actuation force acting on the cord 19.

When the cord 19 is acted on by a driving force, the cord 19 is tensioned by the driving force F which causes the plurality of plunger elements 16 to rotate and become aligned along their longitudinal axes. This is illustrated in FIGS. 5B and 5C.

In addition, as shown in FIGS. 5A to 5C, from the cross-sectional view the plurality of plunger elements 16 have rounded corners around their edges. The technical advantages associated with this particular feature are described in the above with respect to FIG. 2.

A securing means 26 is provided at one end of the cord 19 in order to secure the plurality of plunger elements 16 in the cord 19. The other end of the cord 19 is fixed to a drive spring 24 that is held in a compressed state by an activation arrangement 25.

When the activation arrangement 25 is activated, as shown in FIG. 5B, the drive spring 24 decompresses and releases stored spring energy so as to exert a driving force on the cord 19. The cord 19 is tensioned by the driving force, which then causes the plurality of plunger elements 16 to rotate and become aligned along their longitudinal axes, as shown in FIG. 5C.

As the diameters of the plurality of plunger elements 16 are larger than their heights, when the plurality of plunger elements 16 become more and more aligned along their longitudinal axes, the piston 23 is pushed towards the distal end of the housing 11 so as to allow more room within the syringe 18 to accommodate the aligned plurality of plunger elements 16. At the same time, the movement of the piston 23 displaces the liquid medicament to a user through the hollow injection needle 17.

In the present embodiment, a projection is provided at a side wall of the housing 11 of the injector device 10 so as to limit decompression of the drive spring 24.

Figure 6A:
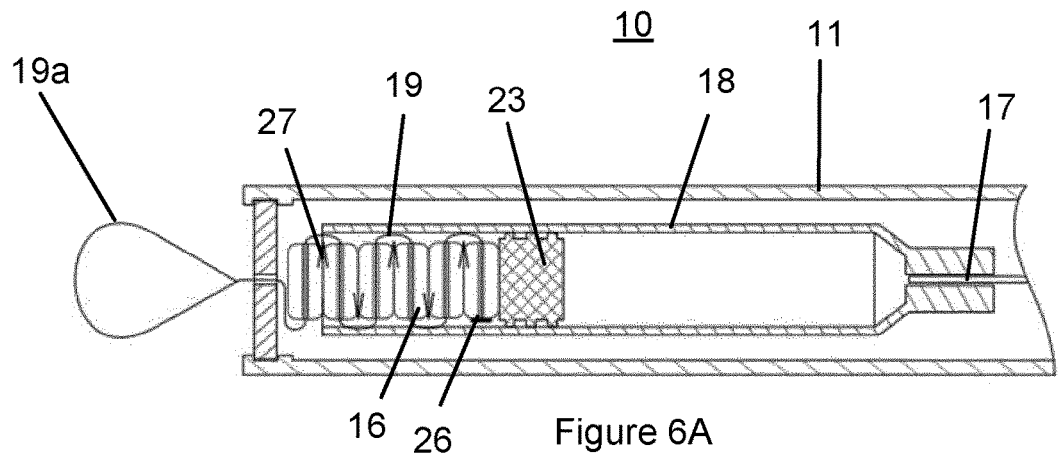
FIGS. 6A, 6B, and 6C are cross-sectional views of an auto-injector device according to a third embodiment in an initial state, an intermediate state, and a final state.
Figure 6B:
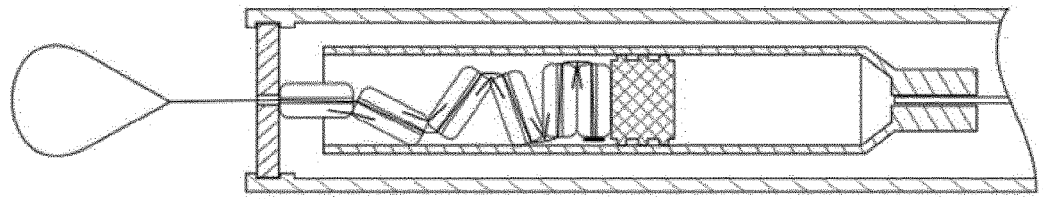
Figure 6C:
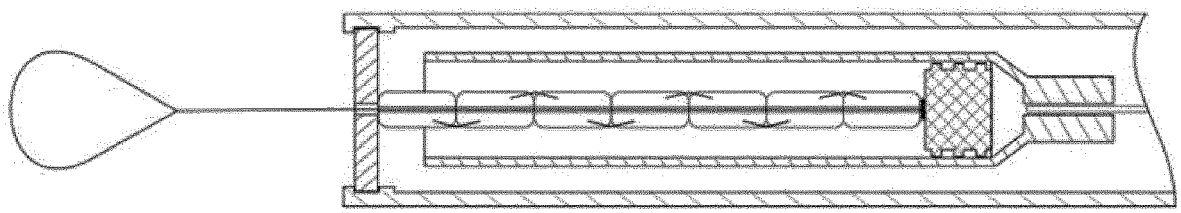

FIG. 6A is a cross-sectional view of an auto-injector device in an initial state, according to a third embodiment. FIGS. 6B and 6C are cross-sectional views of the auto-injector device of FIG. 6A in an intermediate state and a final state respectively.

The third embodiment as illustrated in FIGS. 6A to 6C is similar to the first embodiment as shown in FIGS. 2 to 4. In the third embodiment, each of the plurality of plunger elements 16 are connected by a plurality of elastic elements 27. Specifically, each of the plurality of elastic elements 27 connects two adjacent plunger elements at their respective contacting edges. In the initial state as shown in FIG. 6A, the plurality of elastic elements 27 are in a neutral unstressed state.

Similar to the first embodiment, in the third embodiment the auto-injector device 10 comprises a housing 11. The housing 11 is arranged to contain a syringe 18 having a hollow injection needle 17 and a piston 23 for sealing the syringe 18 and displacing liquid medicament 16 that is contained within the syringe 18. The housing 11 comprises a proximal end and a distal end intended to be applied against an injection site during injection of the liquid medicament. In the present embodiment, the distal end of the housing 11 comprises an orifice for exposing the hollow injection needle 17.

A plurality of plunger elements 16 are arranged along a length of the syringe 18 between the proximal end of the housing 11 and the piston 23, each of the plurality of plunger elements 16 having a longitudinal axis and comprising a longitudinal hole. In the present embodiment, each of the plurality of plunger elements 16 is circular disc-shaped in order to conform to the cylindrical shape of the syringe 18. The holes in each of the plurality of plunger elements 16 are arranged longitudinally (i.e. along a diameter, across the center) in the circular disc-shaped plunger element.

In addition, as shown in FIGS. 6A to 6C, from the cross-sectional view the plurality of plunger elements 16 have rounded corners around their edges. The technical advantages associated with this particular feature are described in the above with respect to FIG. 2.

A cord 19 is threaded through the longitudinal holes of the plurality of plunger elements 16 so as to connect the plurality of plunger elements 16. The cord 19 is made of generally inextensible or inelastic material, such as surgical steel, piano wire or kite line, so as to allow the plurality of plunger elements 16 to exist in the initial state in which they are in a stacked arrangement as shown in FIG. 6A, i.e. their longitudinal axes are each perpendicular to an axis of the syringe 18 without applying any significant force to the piston 23, in the absence of any actuation force acting on the cord 19.

When the cord 19 is acted on by a driving force, the cord 19 is tensioned by the driving force which causes the plurality of plunger elements 16 to rotate and become aligned along their longitudinal axes. This is illustrated in FIGS. 6B and 6C.

A securing means 26 is provided at one end of the cord 19 in order to secure the plurality of plunger elements 16 in the cord 19. In the present embodiment, the securing means 26 is an end tab which is larger than an opening of a longitudinal hole of the plurality of plunger elements 16.

As shown in FIGS. 6A to 6C, a loop 19a is provided at the other end of the cord 19 as a simplified representation of a driving force that is provided to act on the cord 19 towards the proximal end of the housing 11.

It is to be understood that the loop 19a as illustrated in FIGS. 6A to 6C is merely a simplified representation and in some alternative embodiments it may be replaced by any driving actuator that could provide a driving force for acting on the cord 19.

As the cord 19 is tensioned by the driving force, the plurality of plunger elements 16 become aligned along their longitudinal axes, starting with the plunger element 22 that is closest to the proximal end of the housing 11. In the present embodiment, as the plurality of plunger elements 15 become more and more aligned along their longitudinal axes, the plurality of elastic elements 27 becomes more and more stretched, as shown in FIGS. 6B and 6C.

Since the diameters of the plurality of plunger elements 16 are larger than their heights, when the plurality of plunger elements 16 become more and more aligned along their longitudinal axes, the piston 23 is pushed towards the distal end of the housing 11 so as to allow more space within the syringe 18 to accommodate the plurality of plunger elements 16 that are becoming increasingly aligned along their axes. At the same time, the movement of the piston 23 displaces the liquid medicament to a user through the hollow injection needle 17.

After the injection process is complete, the driving force on the loop 19a may be removed such that the cord 19 is released. In the absence of the driving force on the loop 19a and the cord 19, the plurality of plunger elements 16 return to their original state (i.e. the initial state) due to the plurality of stressed elastic elements 27 having the tendency to retract and return to their original neutral unstressed state.

Although not shown in the drawings, the activation arrangement 25 in the present embodiment further comprises a button that extends from a slot formed on a side wall of the housing 11 so as to allow manual operation of the activation arrangement 25 by a user.

In alternative embodiments, the plurality of plunger elements may not comprise longitudinal holes. In these alternative embodiments, each of the plurality of plunger elements may be connected by via a elastic element with its adjacent plunger element without having a cord that is threaded through the plunger elements.

In alternative embodiments, the cord may be made of other material instead of those described above (i.e. surgical steel, piano wire or kite line) according to the requirements and dimensions of the auto-injector device. It is preferred that the cord is made of inductile material.

In some embodiments, the activation arrangement may be implemented as an electrical activation arrangement. For example, the activation arrangement may comprise an electric motor arranged to wind the cord during acting on of the cord. In these embodiment, the auto-injector device may be a reusable auto-injector device or an auto-injector device that allows multiple usage, because in embodiments where the activation arrangement is electrically driven, the driving force provided by the activation arrangement may be released after an injection has been performed such that the plurality of plunger elements return to the initial stacked state.

In alternative embodiments, the activation arrangement may be provided in other physical forms instead of a button.

For example, in such embodiments the activation arrangement may be a switch provided on the side wall of the housing.

In alternative embodiments, instead of circular disc-shape, the plurality of plunger elements 16 may adopt different shapes according to different requirements, e.g. the shape of the syringe, material costs, etc. For example, the plurality of plunger elements may adopt a spherical shape or a cylindrical shape.

Moreover, in alternative embodiments, instead of rounded corners, the plurality of plunger elements may have chamfered or beveled corners so as to achieve a greater angle θ between the moment arm r (i.e. the distance from the pivot point to the point where the driving force from the cord F acts) and the driving force F.

Although claims have been formulated in this application to particular combinations of features, it should be understood that the scope of the disclosure of the present subject matter also includes any novel features or any novel combinations of features disclosed herein either explicitly or implicitly or any generalization thereof, whether or not it relates to the same subject matter as presently claimed in any claim and whether or not it mitigates any or all of the same technical problems as does the present subject matter. The applicant hereby gives notice that new claims may be formulated to such features and/or combinations of features during the prosecution of the present application or of any further application derived therefrom.

Although a few embodiments have been shown and described, it would be appreciated by those skilled in the art that changes may be made in these embodiments without departing from the principles of the disclosure, the scope of which is defined in the claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codable amino acids, or amino acids, including non-codable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that can be useful include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

What is claimed is:

1. An auto-injector for delivering a liquid medicament comprising:
   a housing arranged to contain a syringe and a piston for sealing the syringe and displacing the medicament, the housing having a proximal end and a distal end intended to be applied against an injection site, wherein the syringe comprises:
   a plunger arrangement comprising a plurality of plunger elements arranged along a length of the syringe between the proximal end of the housing and the piston, each of the plurality of plunger elements having a longitudinal axis; and
   an inextensible cord arranged to connect the plurality of plunger elements,
   wherein the plunger elements are initially in an unaligned arrangement and are configured such that when the inextensible cord is tensioned by a driving force, the plunger elements become aligned along their longitudinal axes and thereby extend the length of the plunger arrangement, and
   wherein the extension of the length of the plunger arrangement pushes the piston towards the distal end to displace the medicament.

2. The auto-injector of claim 1, wherein each of the plurality of plunger elements comprises a longitudinal hole, and the inextensible cord is threaded through the longitudinal holes of the plurality of plunger elements to connect the plurality of plunger elements.

3. The auto-injector of claim 1, wherein the plurality of plunger elements are in a stacked arrangement in an initial state.

4. The auto-injector of claim 1, further comprising a driving actuator connected to the inextensible cord so as to provide the driving force for acting on the inextensible cord.

5. The auto-injector of claim 4, wherein the driving actuator comprises a drive spring releasably compressed by an activation arrangement, and wherein when upon activating the activation arrangement the drive spring is released such that it decompresses to provide the driving force for acting on the inextensible cord.

6. The auto-injector of claim 5, wherein the drive spring and the activation arrangement are arranged at a side wall of the housing.

7. The auto-injector of claim 6, further comprising a projection provided at the side wall of the housing arranged to limit decompression of the drive spring.

8. The auto-injector of claim 6, further comprising a slot provided at the side wall of the auto-injector through which the activation arrangement protrudes, so as to allow manual operation of the activation arrangement.

9. The auto-injector of claim 5, wherein the activation arrangement comprises an electric motor.

10. The auto-injector of claim 9, wherein the electric motor is arranged to wind the inextensible cord during acting on of the inextensible cord.

11. The auto-injector of claim 1, wherein each of the plurality of plunger elements has a circular disc shape.

12. The auto-injector of claim 1, wherein edges of the plurality of plunger elements adjacent the ends of a plurality of longitudinal holes are rounded or chamfered.

13. The auto-injector of claim 1, wherein adjacent plunger elements in the plurality of plunger elements are connected by a plurality of elastic elements, the plurality of elastic elements are arranged to stretch as the plunger elements become aligned along their axes.

14. The auto-injector of claim 1 including a medicament included in the syringe.

15. A method of actuating an auto-injector having a plurality of plunger elements arranged with longitudinal axes arranged generally laterally to a longitudinal axis of the auto-injector, comprising the step of: applying a force in the longitudinal direction of the auto-injector to at least one of the plurality of plunger elements to cause realignment of the at least one of the plurality of plunger elements so that the longitudinal axis of the plunger element is aligned generally parallel to the longitudinal axis of the auto-injector.

16. The auto-injector of claim 1, wherein a securing means is provided at one edge of the inextensible cord to secure the plurality of plunger elements in the inextensible cord.

17. The auto-injector of claim 1, wherein the plurality of plunger elements return to their initially unaligned arrangement when the driving force is released from the inextensible cord.

18. The auto-injector of claim 5, wherein the activation arrangement further comprises a button that extends from a slot formed on a side wall of the housing.

19. The auto-injector of claim 1, wherein all longitudinal axes of the plunger elements are co-linear with each other in the aligned arrangement.

20. The auto-injector of claim 1, wherein all longitudinal axes of the plunger elements are substantially parallel to each other in the unaligned arrangement.

* * * * *